(12) United States Patent
Bischoff et al.

(10) Patent No.: US 6,767,747 B1
(45) Date of Patent: Jul. 27, 2004

(54) MEASURING PROBE AND METHOD FOR MEASURING THE CONCENTRATION OF AGENTS IN GASES AND/OR LIQUIDS

(76) Inventors: Gerlinde Bischoff, Carl-von-Ossietzky-Strasse 12, D-06114 Halle / Saale (DE); Robert Bischoff, Carl-von-Ossietzky-Strasse 12, D-06114 Halle / Saale (DE)

(*) Notice: Subject to any disclaimer, the term of this patent is extended or adjusted under 35 U.S.C. 154(b) by 0 days.

(21) Appl. No.: 09/806,736
(22) PCT Filed: Oct. 30, 1999
(86) PCT No.: PCT/DE99/03547
§ 371 (c)(1), (2), (4) Date: Apr. 4, 2001
(87) PCT Pub. No.: WO00/34764
PCT Pub. Date: Jun. 15, 2000

(30) Foreign Application Priority Data

Dec. 10, 1998 (DE) .......................................... 198 56 885

(51) Int. Cl.⁷ ...................... G01N 27/416; G01N 25/18; G01N 27/00; G01N 33/48; G01N 27/26
(52) U.S. Cl. .......................... 436/151; 436/43; 436/149; 422/50; 422/83; 422/88; 422/68.1; 204/416; 204/418
(58) Field of Search .......................... 436/43, 149, 151; 422/50, 83, 88, 68.1, 82.01, 82.02; 204/416, 418; 250/336.1

(56) References Cited

U.S. PATENT DOCUMENTS 5,572,027 A * 11/1996 Tawil et al. .............. 250/336.1

6,004,442 A * 12/1999 Choulga et al. ............ 204/416
6,200,444 B1 * 3/2001 Ahlers et al. ............... 204/418

FOREIGN PATENT DOCUMENTS

| DE | 44 37 274 | | 4/1996 |
|---|---|---|---|
| EP | 0 328 108 | | 8/1989 |
| GB | 2 204 408 | | 11/1988 |
| GB | 2 208 006 | | 2/1989 |
| WO | 89/08713 | | 9/1989 |
| WO | WO 96/12176 | * | 4/1996 |

* cited by examiner

Primary Examiner—Jill Warden
Assistant Examiner—Brian Sines
(74) Attorney, Agent, or Firm—Michael J. Striker

(57) ABSTRACT

The measuring probe (1) for detecting agents in a gaseous or liquid medium and/or measuring their concentrations includes a sensor-active solid layer (4) that reacts to adsorption of an agent from a gas or liquid by changing its electrical properties; a liquid covering film (7) formed from the gas or liquid, such as a water film, which covers the sensor-active solid layer (4), and a plurality of electrodes (2) arranged in electrical contact with the sensor-active solid layer (4) for electrical measurement of conductivity changes due to presence of the agents in the gas or liquid. According to the measurement procedure of the invention, the measuring probe surface is doped reversibly by adsorption with the agents to form an active surface that influences the measured electrical conductance and the electrical conductance is measured. Various measured partial conductances, in particular, of the solid layer (4), the liquid covering film (7) and the active surface (8) formed between both of these, are included in the total conductance without compensation.

2 Claims, 2 Drawing Sheets

Figure 1:
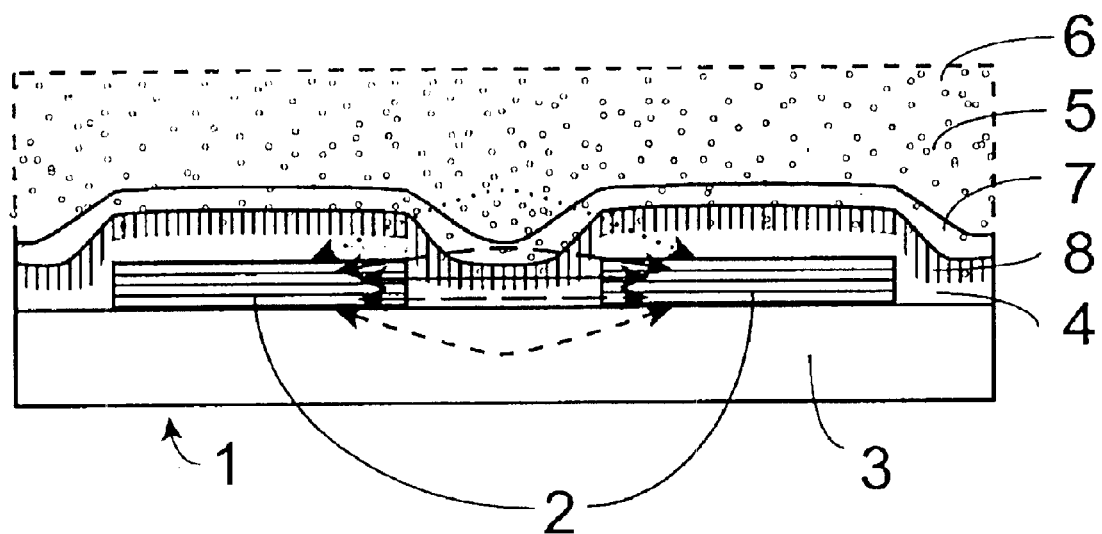

MEASURING PROBE AND METHOD FOR MEASURING THE CONCENTRATION OF AGENTS IN GASES AND/OR LIQUIDS

The invention designates a measuring probe of a measuring device and an associated measurement procedure for the measurement of the concentration of agents in gases and/or liquids. To do this, the measuring device uses the change in electrical characteristics. To conduct the measurement, the substances to be examined are placed in contact with the surface of the measuring device. The substance changes the conductivity, depending on its concentration, of the surface of the measuring device.

It is known, that the concentration of various agents can be determined with the aid of resistance measurements. For example, the international patent classification (IPC), G01N 27/00, describes the analysis of materials through the application of electrical methods. Under G01N 27/12 special resistance studies are considered, which show the change in the resistance of a solid in relation to the absorption of a liquid. Measuring probes with electrodes are used to do this, which are described in G01N 27/07.

It is also known that such measuring probes of measuring devices consist of two suitably formed electrodes, which are attached to a support, and that the conductivity of a suitable substance is determined between these electrodes as an indirect measurement variable for the determination of the concentration of the substances being examined. Depending on the agents being examined, various often specially optimized substances are used, on which the agents being examined adsorb. In addition, the substance itself also has a certain electrical conductivity, which is changed by the adsorption and physical combination of agents serving as an adsorbate. Organic and inorganic semiconductor materials are used as suitable materials for this purpose, since the relative change of the conductivity due to the adsorption of these agents is sufficiently large. For various agents, both small band and broadband substances are known, which function selectively. The change of the electrical conductivity serves to determine the concentration since a monotone relation of this with the concentration exists in the applied measurement area. It is possible to use an oscillating field for the measurement of the change in the electrical conductivity and to apply its additional parameters such as specific complex loss angle as an additional aid for the evaluation.

By using a suitable design of the electrodes, the usable conductivity range can be represented by a suitable conductance of the measuring probe. By means of a suitable arrangement of the surface, such as pores, between the electrodes, the proportional influence of the adsorption on the part of the substance used for the measurement can be changed. The adsorption time is determined, in particular, by the type of substance layer and the substance temperature.

A number of such measuring probes for the determination of the concentration of various agents in gases are manufactured with organic semiconductor material, preferably polymers, on ceramic supporting materials. Due to the high humidity and the high surface tension of water, the substances of such measuring probes are coated with a thin water film in a normal climate. Due to its own conductivity, this results in a total conductivity of the measuring device, which is about one magnitude above that of the substances used. In order to prevent an incorrect measurement due to the absorption of water, such measuring probes are equipped with a heating element or a separate heating unit, which heats the substance so that the moisture film evaporates completely. These measuring probes necessarily function with higher temperatures compared to the surroundings and primarily above 150° C. The useful measurement range, with respect to the concentration of the agents, normally runs from a minimum of 1 part per million (ppm) to a saturation concentration of the agent being determined. Within this measurement range and with increasing concentration, there is a monotone increasing conductance of the measuring probe, which, based on previous calibration, can be converted into the concentration of the agent being examined.

The disadvantage of such sensors is the relatively low sensitivity to very low concentrations for certain agents in U gases and the requirement for heating. Due to this, such measuring probes are more complex and more expensive to manufacture and to operate. In addition, the use of these in the ambient temperature range, for example for a normal climate, is limited.

The specification sheet, EP 0 328 108 A3, describes an electrochemical sensor for the measurement of the concentration of a chemical substance in a solution, where two field-effect transistors (FET) and a reference electrode are arranged on a substrate. A hydrogel as an "electrode" is arranged above the area of the channel of one of the FETs and the reference electrode and enzymes are used for substance detection, which activate the FET through the change of the conductivity in the electrode. The detection of the type and concentration of the substance in the solution is done by means of an evaluation of the signal from the FET.

This sensor can only be used for the determination of relatively high concentrations in the range of a few parts per million for substances in solutions but agents in gases cannot not be determined sufficiently with this method. The concentration of only a few selected substances can be determined in this manner. In addition, the hydrogel for the sensor can be easily and irreversibly contaminated with substances disturbing the measurement and this makes the sensor unusable. Due to the microstructures, expensive technologies from the microelectronics area are needed to manufacture such sensors.

The announcement of the PCT application with the number, WO 89/08713, reveals a method and a device for determining the concentration of certain body fluids. A fluid sample is placed in a sample cell with two electrodes and mixed with an oxidizing agent and a buffer as a redox-system and then the conductivity is read from an ammeter and an evaluation unit and display unit show the concentration of the substance in the body fluid. The conductivity of the sample fluid is also used to turn on the measuring device. The disadvantage of this method is the limitation to liquids, the relative insensitivity with a lower detection range in a concentration of ppm and the arrangement of a reference electrode in the sample cell. This is further development of the measurement arrangement for the determination of the conductivity of liquids.

The purpose of the invention is to develop a measuring probe and an associated measuring process, which results in a sensitive measuring probe, without the above disadvantages, for the detection of agents and their concentration in gases and/or liquids and this is to be done under the most varied of real measuring conditions without additional expenditure and without a heating element.

This purpose is fulfilled by the characteristics listed in patent claim 1 and in patent claim 7. Priority for further developments result from the subclaims.

The essence of the invention is that a measuring probe in the form of a dipole is used to determine the electrical resistance of a sensor-active layer, where a covering film from a liquid such as water is purposely included in the active zone of the measuring probe. The covering film forms over the substance of the sensor-active layer. Based on the covering film, a combination of various partial conductances is available. In particular these are the conductances for the substance, the covering film and for the active surface, which forms between both of these. Molecules of the covering film can also serve as an adsorbate for the agent to be determined in the gas or liquid, in addition to the substance. The adsorption characteristics for certain agents can be optimized by the systematic selection of the liquid for the covering film.

The measurement procedure, according to the invention, is specially designed for the measuring probe according to the invention. The probe operates basically under saturated conditions with respect to the adsorption of the liquid in the diffusion layer. In its basic condition (0% agent+liquid in saturation) there is a comparatively high conductance. The presence of certain agents, depending on the type, results in a hindrance or promotion of mobile charge carries and/or reduces or increases the number of the mobile charge carriers. In this manner, the smallest traces of the gas to be detected have an exponential effect on the electrical conductivity of the measuring probe and reduce or increase the conductivity drastically and the effect of a reversible doping occurs on the surface of the measuring probe. This effect occurs even with relatively small concentrations of the agent to be found and is reinforced with increasing concentration of the agent. With an increasing concentration of the agent, this results in a decreasing or increasing differential conductance of the measuring probe with respect to the basic condition. This conductance can, according to the invention and assuming prior calibration, be used for the calculation of the concentration of the agent to be found. To do this an equivalent circuit diagram for the sensor is used, which represents this an electrical dipole. The complex equivalent variables required for the description in the measurement window correlate primarily with the resistances and the thicknesses of the individual layers.

The advantages of the invention are found particularly in the greater sensitivity of the measurement procedure, compared to measuring probes without a covering film over the substance, by at least two powers of ten and thus the detection limit, for the agent to be found, is in the area of parts per trillion (ppt) of concentration of the agent. Thus, the possibility of conducting measurements under real conditions without additional expenditure exists, for example at room temperature in a normal atmosphere or inside the body of a living organism. Long-term measurements for the continual monitoring of concentrations of certain agents can be carried out without the use of complicated equipment.

The sensor does not require any heating element and thus no temperature equalization or other special measuring conditions.

It is also imaginable that such measuring probes could be combined with other measuring probes in order to, for example through the determination of the temperature and/or humidity, be able to consider the influence of these parameters for the calculations in the process according to the invention.

In addition, it is also imaginable that several such measuring probes could be combined, for example, in an array with various structural dimensions and/or substances in order to include the selective characteristics of the substances in the analysis with respect to certain agents.

Another further development could be that such sensors on supporting material could be integrated directly into the circuit of a controlled semiconductor element such as the base or gate circuit.

Additional possibilities for using the measurement results for concentrations of certain agents occur when these results are transferred to authorized recipients over EDP networks or telecommunications systems.

The invention will be described in more detail as an example of application based on FIG. 1 as the construction principle of the measuring probe and FIG. 2 as the equivalent circuit diagram of the measuring probe.

According to FIG. 1, a measuring probe (1) for agents in gases consists of a pair of electrodes (2), which are partially attached to a supporting material (3), whereby these can be formed as a rise on the surface. There is a suitable solid substance (4) in layers located above this surface structure. In particular this substance is an organic semiconductor in the form of a polymer, which reacts to the adsorption of certain agents (5) with a sufficient change in conductivity. The agents (5) to be analyzed are in a gaseous state (6), which expands as an environment for the measuring probe around the surface of the measuring probe (1). There is also a covering film (7) located between the surface structure of the measuring probe (1) and the gaseous state (6). The film consists of water and the films forms due to the finite humidity of the gaseous state (6). Due to the mutual influence between the substance (4) and the covering film (7) of water, an effective active surface (8) is formed with respect to the change of the conductivity. Molecules of the agent (5) to be found are adsorbed on the surface of the substance (4) and on the molecules of the covering film (7) and at these locations they replace water molecules and change the total conductivity of the sensor.

Figure 2:
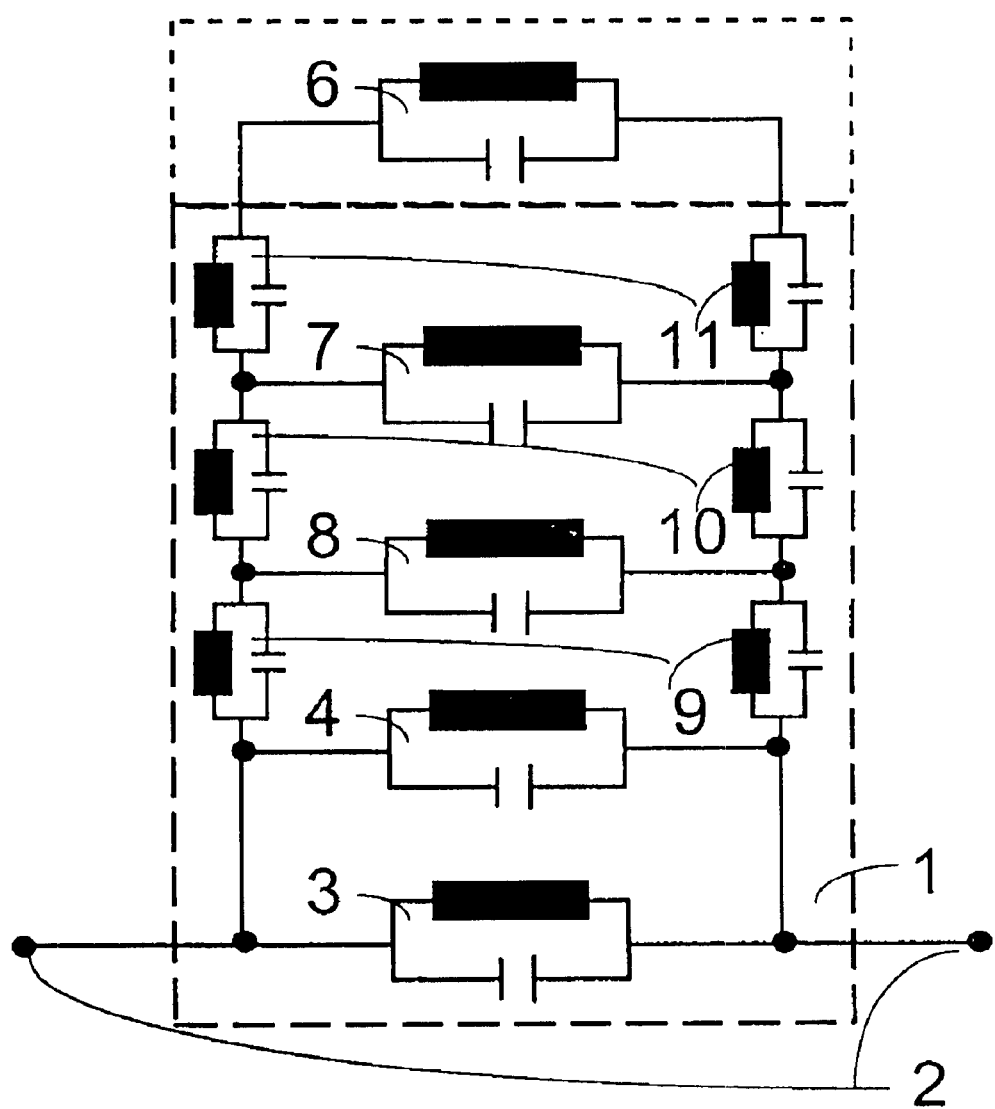

According to FIG. 2, an equivalent circuit diagram can be assumed for the individual layers and thicknesses of the measuring probe in the form of a resistance network, which represents the measuring probe as an electrical dipole in a permissible measurement window. Such an equivalent circuit diagram is used primarily as the basis for the calibration of the measuring probe (1) and, based on this, the determination of the concentration of the agents (5) to be analyzed. In particular, this allows a non-linear representation by fiducial values, which are essentially independent of one another and correlate strongly with the design of the measuring probe. By using complex equivalent variables in the form of resistances, the behavior in the electrically oscillating field is also described. A parallel connection between an effective resistance and a reactive impedance characterizes the layer resistances for the supporting material (3), the substance (4), the active surface (8), the covering film (7) of water, the gaseous state (6) and an equivalent resistance I 9, which is essentially dependent on the thickness of the electrodes (2) and the substance (4); an equivalent resistance II 10, which is essentially dependent on the thickness of the active surface (8) and an equivalent resistance III 11, which is essentially dependent on the characteristics of the covering film (7). The thickness of the covering film (7) out of, for example, water is essentially dependent on the temperature. The individual layer resistances are connected in parallel and the equivalent resistances (9, 10, 11) are arranged on both sides between the layer resistances of substance (4), the active surface (8), of the covering film (7) and the gaseous state (6).

Using conventional measurement and evaluation units, the change of the total conductivity of the sensor is registered through lines from the electrodes (2) and the change is recorded and evaluated to determine the concentration of the agent.

Reference Symbols Used

1. Measuring probe
2. Electrodes
3. Supporting material
4. Substance
5. Agent
6. Gaseous state
7. Covering film
8. Active surface
9. Equivalent resistance I
10. Equivalent resistance II
11. Equivalent resistance III

What is claimed is:

1. A measurement procedure for detecting agents in a gaseous or liquid medium and/or measuring concentrations of said agents in said gaseous or liquid medium, said procedure comprising the steps of:

a) providing a measuring probe comprising a sensor-active solid layer (4) which reacts to adsorption of agent molecules from a gas or liquid containing the agent molecules by changing electrical properties of the sensor-active solid layer (4); a liquid covering film (7) arranged between said gas or liquid and said sensor-active solid layer (4) so as to cover said sensor-active solid layer (4), said liquid covering film (7) being formed from said gas or liquid; and a plurality of said electrodes (2) arranged in contact with said sensor-active solid layer (4) for measuring electrical conductance changes due to presence of said agent molecules in said gas or liquid;

b) doping a surface of the measuring probe (1) reversibly with said agent molecules by adsorbing said agent molecules on said surface, so that an active surface is formed, whereby said electrical conductance changes due to the presence of said agent molecules in said gas or liquid occur;

c) measuring said electrical conductance changes with the measuring probe provided in step a), wherein total electrical conductance measured by the measuring probe comprises partial conductances of the solid layer (4), the liquid covering film (7), the active surface (8) and the gas or liquid, without compensation; and d) after prior calibration, determining the agents and/or the concentrations of the agents from said electrical conductance changes measured with said measuring probe.

2. The measurement procedure as defined in claim 1, further comprising transmitting measurement results of said measuring over EDP networks and/or be telecommunications devices to authorized recipients.

* * * * *